US008716299B2

(12) United States Patent
Mohapatra et al.

(10) Patent No.: US 8,716,299 B2
(45) Date of Patent: May 6, 2014

(54) XIAP-TARGETED PROSTATE CANCER THERAPY

(75) Inventors: Subhra Mohapatra, Tampa, FL (US); W. Jack Pledger, Odessa, FL (US)

(73) Assignee: University of South Florida, Tampa, FL (US)

( * ) Notice: Subject to any disclaimer, the term of this patent is extended or adjusted under 35 U.S.C. 154(b) by 1418 days.

(21) Appl. No.: 11/306,241

(22) Filed: Dec. 20, 2005

(65) Prior Publication Data

US 2007/0027169 A1 Feb. 1, 2007

Related U.S. Application Data

(60) Provisional application No. 60/593,188, filed on Dec. 20, 2004.

(51) Int. Cl.
*A61K 31/52* (2006.01)
*A01N 43/90* (2006.01)

(52) U.S. Cl.
USPC ........................................... 514/263.2

(58) Field of Classification Search
USPC ........................................... 514/263.2
See application file for complete search history.

(56) References Cited

U.S. PATENT DOCUMENTS

| | | | |
|---|---|---|---|
| 6,221,873 B1 | 4/2001 | Havlicek et al. | |
| 2002/0012703 A1* | 1/2002 | Singh | 424/488 |
| 2002/0187519 A1* | 12/2002 | Helson | 435/7.23 |
| 2003/0125374 A1* | 7/2003 | Altieri et al. | 514/449 |
| 2004/0096436 A1* | 5/2004 | Carson et al. | 424/94.4 |
| 2004/0186118 A1 | 9/2004 | Bryant et al. | |
| 2005/0153991 A1 | 7/2005 | Gianella-Borradori et al. | |

FOREIGN PATENT DOCUMENTS

WO       WO 03024183 A2 *  3/2000

OTHER PUBLICATIONS

Edamatsu et al (CDK inhibitors, roscovitine and olomoucine, synergize with farnesyltransferase inhibitor (FTI) to induce efficient apoptosis of human cancer cell lines, Oncogene (2000) 19, 3059-3068).*
Asgari et al (Int. J. Cancer: 71, 377-382, 1997).*
Kuratsukuri, et al (The Prostate 41:121-126 (1999).*
Stackhouse et al (The Journal of Urology, vol. 162 (Dec. 1999) 2040-2045).*
Phosphorylation/Dephosphorylation: Cyclin-Dependent Kinase (Cdk) Inhibitors, Merck Biosciences UK-Calbiochem-Inhibitors, www.merckbiosciences.co.uk, 2005.

(Continued)

*Primary Examiner* — Benjamin Packard
(74) *Attorney, Agent, or Firm* — Michele L. Lawson; Smith & Hopen, P.A.

(57) ABSTRACT

A treatment for prostate cancer using cyclin-dependent kinase inhibitors is provided. The effects of cyclin-dependent kinase inhibitors on the survival of prostate cancer cells was examined. Roscovitine, R-roscovitine, and CGP74514A were shown to induce the apoptosis of LNCaP and LNCaP-Rf cells, both of which express wild-type p53. The cyclin-dependent kinase inhibitors of the present invention induce the mitochondria-mediated apoptosis of prostate cancer cells by a dual mechanism: p53 accumulation and XIAP depletion.

14 Claims, 5 Drawing Sheets

(56) References Cited

OTHER PUBLICATIONS

Chunrong Yu et al., The Lethal Effects of Pharmacological Cyclin-dependent Kinase Inhibitors . . . , Cancer Research 63, p. 1822-1833, Apr. 15, 2003.

Eric Asselin et al., XIAP Regulates AKT Activity and Caspase-3-dependent Cleavage during Cisplatin-induced Apoptosis . . . , Cancer Research 61, p. 1862-1868, Mar. 1, 2001.

Hiromasa Sasaki et al., Down-Regulation of X-linked Inhibitor of Apoptosis Protein Induced Apoptosis in Chemoresistant . . . , Cancer Research 60, p. 5659-5666, Oct. 15, 2000.

Adams Amantana et al., X-Linked Inhibitor of Apoptosis Protein Inhibition Induces Apoptosis and Enhances . . . , Moleculas Cancer Theraputics, p. 699-707, Jun. 2004.

Cheng Jiang et al., Selenite-induced p53 Ser-15 Phosphyorylation and Caspase-Mediated Apoptosis . . . , Molecular Cancer Therapeutics, p. 877-884, Jul. 2004.

S. Mohapatra et al., Accumulation of p53 and Reductions in XIAP Abundance Promote the Apoptosis of Prostate Cancer Cells, www.ncbi.nlm.nih.gov, www.pubmed.gov.

* cited by examiner

XIAP-TARGETED PROSTATE CANCER THERAPY

CROSS-REFERENCE TO RELATED APPLICATION

This application claims priority to U.S. Provisional Patent Application No. 60/593,188, entitled "XIAP-Targeted Prostate Cancer Therapy", filed Dec. 20, 2004, the contents of which are herein incorporated by reference.

STATEMENT REGARDING FEDERALLY SPONSORED RESEARCH

This invention was made with government support under R01-CA093544 awarded by the National Cancer Institute. The government has certain rights in the invention.

FIELD OF INVENTION

The present invention relates to prostate cancer therapy. More particularly, this invention relates to XIAP-targeted prostate cancer therapy using cyclin-dependent kinase inhibitors.

BACKGROUND OF THE INVENTION

Prostate cancer is the most common malignancy in males in Europe and North America (52). In the United States, more than 200,000 men develop prostate cancer each year, and more than 30,000 men die from prostate cancer each year. In initial stages, prostate cancers are localized and androgen-dependent; in advanced stages, they are invasive, metastatic, and heterogeneous in terms of androgen-dependence. The standard treatment for advanced prostate cancer is androgen ablation. Such treatment induces the apoptosis of androgen-dependent cells and reduces the size of primary and metastatic lesions; however, the surviving androgen-resistant cells typically form aggressive, drug-resistant populations. These observations emphasize the need for effective treatments for advanced prostate cancer.

The purine analogs roscovitine, R-roscovitine (CYC002), and CGP74514A inhibit the activity of cyclin-dependent kinases (CDKs), most notably cdk2, cdk1, and cdk7 (1-3). Roscovitine is the compound 6-benzylamino-2-[(R)-1-ethyl-2-hydroxye-thylamino]-9-isopropylpurine. R-roscovitine refers to the R enantiomer of roscovitine, specifically the compound 2-(1-R-hydroxymethylpropylamino)-6-benzylamino-9-iso-propylpurine. CGP74514A is the compound N-(cis-2-Aminocyclohexyl)-N-(3-chlorophenyl)-9-ethyl-9H-purine-2,6-diamine. cdk2 and cdk1 promote the entry of cells into S phase and mitosis, respectively, and cdk7 facilitates transcription. These inhibitors have been linked to apoptosis, though the mechanisms are unclear (2, 4-9).

Apoptosis requires the activation of a family of cysteine aspartyl proteases termed the caspases (10). Adaptor proteins promote the autocleavage and activation of initiator caspases (e.g., caspase-8 and caspase-9), initiator caspases cleave and activate effector caspases (e.g., caspase-3), and effector caspases induce a multiplicity of events that ultimately result in cell death (e.g., plasma membrane blebbing and DNA fragmentation). There are two apoptosis signaling pathways: the death receptor pathway and the mitochondrial pathway. When active, death receptors interact with adaptor proteins such as FADD and TRADD and activate caspase-8. When damaged, mitochondria release cytochrome c, which associates with the adaptor protein Apaf-1 and activates caspase-9. Most drugs signal apoptosis through the mitochondrial pathway.

Proteins that modulate caspase activity—and thus determine whether cells live or die—include the IAPs (Inhibitor of Apoptosis Proteins) and the Bcl-2 proteins. The IAP family includes cIAP-1, cIAP-2, XIAP, and survivin (11). Of these proteins, XIAP is the most potent. IAPs interact with and inhibit the activity of processed caspases; thus, they function as 'brakes' that can impede the apoptotic process once it begins. IAPs inactivate both initiator and effector caspases; caspase-9 and caspase-3 are IAP targets, whereas caspase-8 is not (12).

The Bcl-2 proteins are critical determinants of mitochondria-dependent caspase activation (13). Some Bcl-2 proteins are apoptotic (e.g., Bax, Bak, and the BH3-only proteins), whereas others are anti-apoptotic (e.g., Bcl-2 and Bcl-$X_L$). Death stimuli activate Bax and Bak, which perforate the outer mitochondrial membrane in a manner dependent on the BH3-only proteins. Although incompletely resolved, Bcl-2 and Bcl-$X_L$ prevent the activation of Bax and Bak by sequestering the BH3-only proteins or by interacting with Bax and Bak.

p53 is a transcription factor that often couples apoptotic signals to changes in the abundance and/or activity of the Bcl-2 proteins (14). It accumulates in cells in response to many chemotoxic drugs, typically as a result of stabilization, and it promotes apoptosis by both transcription-dependent and -independent mechanisms. In the nucleus, p53 transactivates genes encoding apoptotic proteins such as Bax and the BH3-only proteins Noxa and Puma (15-17). When localized to mitochondria, p53 activates Bax and Bak by interacting with Bcl-2 family members (18). The mitochondrial actions of p53 are newly described and incompletely characterized. Given its role as a death signal, it is not surprising that p53 is frequently mutated in human tumors (19).

SUMMARY OF INVENTION

The present invention provides a method for treating prostate cancer in a subject. In one aspect of the invention the method includes the step of administering a cyclin-dependent kinase inhibitor (CDK) inhibitor to a subject in need thereof. In certain aspects of the invention the CDK inhibitor can include CGP74514A, roscovitine and R-roscovitine. In further aspects of the invention the CDK inhibitor is a therapeutically effective amount of roscovitine or a pharmaceutically acceptable salt thereof. The taught method is advantageous where the prostate cancer is advanced prostate cancer characterized by androgen-independence. The taught method is also advantageous where the prostate cancer cells express wild-type p53. In certain aspects the disclosed metholgy provides a CDK inhibitor that induces apoptosis in the prostate cancer cell by p53 accumulation and XIAP depletion.

In further aspects of the invention the CDK inhibitor is administered in combination with a phosphatidylinositol-3 kinase (PI3K) inhibitor. The PI3K inhibitor can be LY294002 or Wortmanin.

In further aspects the disclosed method will include the step of performing androgen ablation therapy.

In another aspect of the invention the CDK inhibitor is administered with at least one additional component which can include a pharmaceutically acceptable carrier, a diluent and an excipient.

In another aspect the present invention provides a method for inducing p53 accumulation and XIAP depletion in a subject having prostate cancer comprising the step of administering a cyclin-dependent kinase inhibitor (CDK) inhibitor to a subject in need thereof, whereby the induction of p53 accumulation and XIAP depletion aids the treatment of prostate cancer characterized by androgen-insensitivity.

In another aspect the present invention provides a method for predicting the sensitivity of a subject to cancer treatment with a purine analog comprising the step of assaying a sample taken from said subject for the presence of p53, wherein the presence of p53 is indicative of a favorable response to the treatment.

BRIEF DESCRIPTION OF THE DRAWINGS

For a fuller understanding of the nature and objects of the invention, reference should be made to the following detailed description, taken in connection with the accompanying drawings, in which:

FIG. 1 shows apoptosis of LNCaP cells by CKIs. (A) LNCaP cells received the indicated concentrations of roscovitine or CGP74514A for 20 hr. Amounts of cytosolic, histone-associated DNA fragments were determined by a cell death detection ELISA. Error bars show standard deviation. bgd: background (buffer only). (B) LNCaP cells received DMSO (control), 25 micro-M roscovitine, or 25 micro-M R-roscovitine for 20 hr. For detection of cells containing cleaved keratin 18 (K18), cells were immunostained with fluorescein-conjugated M30 antibody. For detection of all cells, cells were stained with DAPI. (C) LNCaP cells received DMSO (control, C), 25 micro-M roscovitine (ROS), 5 micro-M CGP74514A (CGP), or 15 micro-M LY294002 (LY) for 20 hr. Amounts of cleaved PARP were determined by Western blotting of cell extracts. Amounts of survivin are unaffected by CKIs (see FIG. 4A) and are shown as a loading control.

FIG. 2 shows apoptosis of LNCaP-Rf cells by CKIs. (A) LNCaP-Rf cells received DMSO (control, C), 25 micro-M roscovitine (ROS), or 5 micro-M CGP74514A (CGP) for 20 hr. Amounts of cleaved PARP were determined by Western blotting of cell extracts. (B) LNCaP-Rf cells received DMSO (control) or 25 micro-M roscovitine for 20 hr. Apoptosis was monitored by keratin 18 (K18) cleavage, as visualized by immunofluorescence using the M30 antibody.

FIG. 3 shows caspase activation and accumulation of cytochrome c in CKI-treated LNCaP cells. (A) LNCaP cells were pretreated with the caspase-9 inhibitor z-LEHD-fmk or the caspase-3 inhibitor z-DEVD-fmk at the indicated concentrations for 1 hr. Roscovitine (ROS) was added to pretreated and non-pretreated (control, C) cultures to a final concentration of 25 micro-M. Cells were harvested 20 hr after addition of roscovitine, and amounts of cytosolic, histone-associated DNA fragments were determined. Error bars show standard deviation. bgd: background (buffer only). (B) LNCaP cells received DMSO (control) or 25 micro-M roscovitine (ROS) for 20 hr. Amounts of cytochrome c in S100 extracts were determined by Western blotting.

FIG. 5 shows the requirement for p53 for efficient apoptosis of CKI-treated prostate cancer cells. (A) LNCaP cells received no addition (NA) or 30 micro-M pifithrin-alpha (PTFalpha) for 24 hr. Cells subsequently received DMSO (control, C) or 25 micro-M roscovitine (ROS) for 16 hr. Amounts of p53 and cleaved PARP were determined by Western blotting of cell extracts. (B) LNCaP and PC3 cells received the indicated concentrations of roscovitine for 20 hr. Amounts of cytosolic, histone-associated DNA fragments were determined by a cell death detection ELISA. Error bars show standard deviation. bgd: background (buffer only). (C) LNCaP and PC3 cells received the indicated concentrations of CGP74514A for 20 hr. Amounts of cleaved PARP and XIAP were determined by Western blotting of cell extracts. (D) LNCaP and DU145 cells received the indicated concentrations of roscovitine for 20 hr. Amounts of cleaved PARP and XIAP were determined by Western blotting of cell extracts.

FIG. 6 shows the requirement for p53 accumulation and XIAP depletion for apoptosis of prostate cancer cells. (A) PC3 cells were infected with adenovirus without insert (Ad) or Ad-p53 (500 virus particles/cell) for 24 hr. Cells then received DMSO (control, C) or 5 micro-M CGP7514A (CGP) for 20 hr. Cell extracts were Western blotted with antibodies to Flag, PARP, and XIAP. (B) PC3 cells were infected with Ad or Ad-p53 (500 virus particles/cell) for 24, 48, or 72 hr. Cell extracts were Western blotted with antibodies to PARP and p53. (C) LNCap and PC3 cells were infected with Ad or Ad-p53 and co-infected with Ad-siXIAP (+) or control adenovirus (!) for 40 hr. Cell extracts were Western blotted with antibodies to p53, PARP, and XIAP. LNCaP cells received adenovirus at 500 virus particles/cell. PC3 cells received adenovirus at 200 virus particles/cell. (D) LNCaP cells were infected with Ad or adenovirus encoding XIAP (Ad-XIAP) (500 virus particles/cell) for 40 hr. Cells then received DMSO (control, C) or 25 micro-M roscovitine (ROS) for 12 hr. Cell extracts were Western blotted with antibodies to Flag and PARP.

DETAILED DESCRIPTION OF THE PREFERRED EMBODIMENT

Our studies examined the effects of roscovitine, R-roscovitine, and CG74514A on the survival of LNCaP cells, which are androgen-dependent prostate cancer cells that express wild-type p53. We show that these inhibitors induce the apoptosis of LNCaP cells by a dual mechanism: they increase the abundance of p53, and they reduce the abundance of XIAP. Importantly, we also show that ectopic expression of p53 coupled with depletion of endogenous XIAP results in the death of androgen-independent prostate cancer cells that lack p53 function. Androgen independence is characteristic of advanced prostate tumors, which are typically both metastatic and drug-resistant. Thus, our findings offer a potential means of eradicating a prevalent and often fatal form of cancer.

Toward the goal of developing effective treatments for prostate cancers, we examined the effects of cyclin-dependent kinase inhibitors on the survival of prostate cancer cells. We show that roscovitine, R-roscovitine, and CGP74514A (collectively referred to as 'CKIs' or 'CDK inhibitors") induce the apoptosis of LNCaP and LNCaP-Rf cells, both of which express wild-type p53. Apoptosis required caspase-9 and caspase-3 activity, and cytochrome c accumulated in the cytosol of CKI-treated cells. Amounts of p53 increased substantially in CKI-treated cells, whereas amounts of the endogenous caspase inhibitor XIAP decreased. CKIs did not appreciably induce the apoptosis of LNCaP cells treated with pifithrin-alpha, which prevents p53 accumulation, or of prostate cancer cells that lack p53 function (PC3 and DU145). Ectopic expression of p53 in PC3 cells for 44 hr did not reduce XIAP abundance or induce apoptosis. However, p53-expressing PC3 cells readily apoptosed when exposed to CKIs or when depleted of XIAP by RNA interference. These findings show that CKIs induce the mitochondria-mediated apoptosis of prostate cancer cells by a dual mechanism: p53 accumulation and XIAP depletion. They suggest that these events in combination may prove useful in the treatment of advanced prostate cancers. We also propose a method for treating prostate cancer in a subject comprising the steps of administering a cyclin-dependent kinase inhibitor (CDK) inhibitor; and performing p53 gene therapy. AdWTp53 vector, a toll for performing p53 gene therapy, has been shown to exhibit a potent inhibitory effect on the growth of all of human metastatic prostate cancer cells, and both cytostatic and cytotoxic effects of AdWTp53 have been observed. (37) These observations are herein extended to the use in a combination therapy with roscovitine.

As used herein, a "therapeutically effective amount" is a concentration, quantity, or level of composition that can attain a particular medical end, such as control or destruction of cancer cells or induce apoptosis in tumorigenic cells. It is an amount sufficient to effect a beneficial or desired clinical result, particularly the generation of a noticeable improvement in clinical condition. In terms of clinical response for subjects bearing a neoplastic disease, a therapeutically effective amount is an amount sufficient to palliate, ameliorate, stabilize, reverse or slow progression of the disease, or otherwise reduce pathological consequences of the disease.

As used herein, an amount or a dosage "effective to induce apoptosis" is the amount, dose, or quantity of a composition which is effective to induce cell death.

Prodrugs

The invention further includes agents of the present invention in prodrug form. Such prodrugs are generally compounds wherein one or more appropriate groups have been modified such that the modification may be reversed upon-administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, intravescical, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, intravescically, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose. In a particularly preferred embodiment, the combination or pharmaceutical composition of the invention is administered intravenously.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.1 to 30 mg/kg body weight, such as from 0.1 to 10 mg/kg, more preferably from 2 to 20 mg/kg body weight.

Roscovitine is typically administered from about 0.05 to about 5 g/day, preferably from about 0.4 to about 3 g/day. Roscovitine is preferably administered orally in tablets or capsules. The total daily dose of roscovitine can be administered as a single dose or divided into separate dosages administered two, three or four time a day.

Combinations

In one preferred embodiment of the invention, one or more CKIs is administered in combination with one or more a phosphatidylinositol-3 kinase (PI3K) inhibitors. In such cases, the compounds of the invention may be administered consecutively, simultaneously or sequentially with the one or more other PI3K inhibitors.

It is known in the art that many drugs are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining drugs are that it may promote additive or possible synergistic effects through biochemical interactions and also may decrease the emergence of drug resistance which would have been otherwise responsive to initial treatment with a single agent.

Beneficial combinations may be suggested by studying the activity of the test compounds with agents known or suspected of being valuable in the treatment of a particular disorder. This procedure can also be used to determine the order of administration of the agents, i.e. before, simultaneously, or after delivery.

This invention is further illustrated by the following examples which should not be construed as limiting. The contents of all references, patents and published patent applications cited throughout this application, as well as the figures, are incorporated herein by reference.

Example 1

Characterization of the XIAP-Targeted Prostate Cancer Therapy

Materials and Methods

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 3d ed. (2001) Cold Spring Harbor Laboratory Press, Cold Spring Harbor, N.Y. and Ausubel et al., Short Protocols in Molecular Biology (1999) 4th Ed, John Wiley & Sons, Inc.

Cell Culture and Reagents.

The human prostate cancer cell lines LnCaP, PC3, and DU145 were provided by Dr. Wenlong Bai (University of South Florida). LnCaP-Rf cells were provided by Dr. Donald Tindall (Mayo Clinic). LnCaP and DU-145 cells were cultured in RPMI 1640 containing 10% fetal calf serum. PC3 cells were cultured in DMEM containing 10% fetal calf serum. LNCaP-Rf cells were cultured in RPMI 1640 containing 10% charcoal-stripped fetal calf serum. All experiments were performed on growing cells in medium containing 10% fetal calf serum.

Stocks of roscovitine, R-roscovitine, and CGP74514A were prepared in DMSO. Roscovitine, LY294002, and pifithrin-α were purchased from Calbiochem. R-roscovitine, z-DEVD-fmk, and z-LEHD-fmk were obtained from Alexis Biochemicals. CGP74514A was purchased from Sigma. Antibodies were obtained from Cell Signaling (Bad, PARP, p53), Santa Cruz Biotechnology (Bax), BD Transduction Laboratories (XIAP, Bcl-$X_L$), Alpha Diagnostic (survivin), Sigma (β-actin, Flag), Upstate (Bak), Neomarker (p21$^{Cip1}$), and Oncogene (PUMA).

Keratin 18 Cleavage.

Immunocytochemistry using the M30 antibody to the keratin 18 cleavage product was performed according to the instructions of the manufacturer (Roche). Twenty hours after plating in chamber slides, cells were incubated with roscovitine, R-roscovitine, CGP74514A, or DMSO (vehicle control). After incubation, cells were fixed in ice-cold methanol at 20° C. for 30 min and incubated with FITC-conjugated M30 antibody for 60 min at room temperature. Cells were mounted with Vectashield containing DAPI.

DNA Fragmentation.

DNA fragmentation was determined using a photometric enzyme-linked immunoassay (Cell Death Detection ELISA kit, Roche) as specified by the manufacturer. Cells in 96-well plates were incubated in triplicate with roscovitine, R-roscovitine, CGP74514A, or DMSO and lysed for 30 min at room temperature. Cell lysates were incubated with biotin-conjugated anti-histone antibody and peroxidase-conjugated anti-DNA antibody on streptavidin-coated microtiter plates for 2 hr at room temperature. After incubation with ATBS substrate for development of color, absorbance was read on a spectrophotometer at 405 nm against ABTS solution as the blank. For background determination, lysis buffer was used instead of cell lysate.

Preparation of S100 Extracts.

Cells were washed in ice-cold PBS, resuspended in an isotonic mitochondrial buffer (210 mM mannitol, 70 mM sucrose, 1 mM EDTA, 10 mM Hepes, pH 7.5, and a protease inhibitor cocktail (Sigma)), and homogenized in a Dounce homogenizer. The heavy membrane fraction was removed by two successive centrifugations, the first at 1000 H g for 10 min and the second at 10,000 H g for 10 min. To obtain the S100 fraction, the supernatant was centrifuged at 100,000 H g for 90 min.

Western Blotting.

Cells were rinsed with PBS and lysed in a buffer containing 50 mM Hepes, pH 7.5, 150 mM NaCl, 1 mM EDTA, 1 mM EGTA, 10% glycerol, 0.5% NP-40, 1 mM dithiothreitol, 0.1 mM phenylmethylsulfonyl fluoride, 2.5 micro-g/ml leupeptin, 0.5 mM NaF, and 0.1 mM $Na_3VO_4$. After a 30 min incubation, insoluble material was removed by centrifugation. Cell extracts normalized for amount protein were resolved by SDS-PAGE and transferred to nitrocellulose membranes. Blots were blocked in PBS containing 0.05% Tween and 5% instant milk and incubated with antibody in PBS containing 0.05% Tween for 2 hr at room temperature. Proteins recognized by the antibody were detected by enhanced chemiluminescence using a horseradish peroxidase-coupled secondary antibody as specified by the manufacturer (Pierce).

Preparation of Adenoviruses Encoding p53, XIAP, and XIAP siRNA.

For preparation of XIAP siRNA, a double-stranded oligonucleotide (5'-GGC AGG TTG TAG ATA TAT CAG CTC GAG CTG ATA TAT CTA CAA CCT GCC CTT TTT G-3' [SEQ ID NO: 1]) was subcloned into pBluescript-U6 (provided by Dr. Yang Shi, Harvard University). The functionality of the resultant plasmid was ascertained by transient transfection of 293 cells. pBluescript-U6 with and without insert was digested with Xba1 to remove the U6 promoter (used for production of control virus) and the U6 promoter plus the XIAP siRNA sequence. Excised DNA was subcloned into the pAdTrack shuttle vector. Shuttle vectors were recombined with pAdEasy-1 according to the instructions of the manufacturer (Stratagene). 293 cells were transiently transfected with pAdEasy-1 to produce control adenovirus and adenovirus encoding XIAP siRNA. Viruses were expanded, purified by CsCl banding, and titered.

Adenovirus encoding Flag-XIAP or Flag-p53 (Pro 72 variant) was prepared using the pShuttle-CMV shuttle vector (Stratagene) and pAdEasy-1. Control virus was obtained by recombination of pShuttle-CMV without insert and pAdEasy-1.

Results

CKIs Induce the Apoptosis of LNCaP Cells and LNCaP-Rf Cells.

Roscovitine, R-roscovitine, and CGP74514A are referred to collectively as CKIs (for CDK inhibitors). Consistent with their inhibitory effects on cdk2 and cdk1 activity, CKIs blocked cell cycle progression when added to exponentially growing LNCaP cells. Less than 5% of cells were in S phase 20 hr after exposure to CKIs, as compared with ~40% of control (vehicle-treated) cells (data not shown). CKI-treated cells accumulated in both G1 and G2/M.

Figure 1:
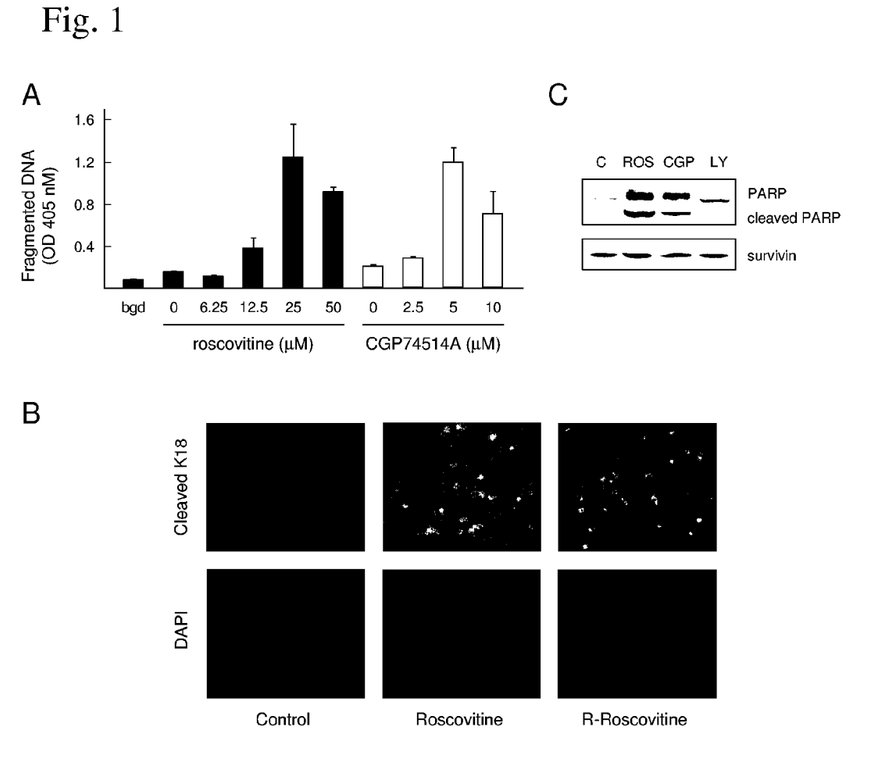

As indicators of apoptosis, we monitored the effects of CKIs on DNA fragmentation and caspase activation in LNCaP cells. All experiments were performed on proliferating cells in serum-supplemented medium. Amounts of cytosolic, histone-associated DNA fragments were quantified by a photometric enzyme-linked immunoassay. As shown in FIG. 1A, DNA fragmentation was minimal in control cells and was 6- to 8-fold greater in cells receiving 25 micro-M roscovitine or 5 micro-M CGP74514A for 20 hr.

Caspase activity was indirectly assayed by monitoring the cleavage of two endogenous caspase substrates, keratin 18 and poly(ADP-ribose)polymerase (PARP). The M30 antibody specifically recognizes cleaved keratin 18 (20), and >30% of cells receiving 25 micro-M roscovitine or 25 micro-M R-roscovitine for 20 hr were M30-positive (FIG. 1B). All control cells were M30-negative. Western blotting showed PARP cleavage in cells exposed to roscovitine or CGP74514A for 20 hr (FIG. 1C). PARP was not cleaved in control cells or in cells exposed to LY294002, an inhibitor of phosphoinositol 3-kinase (PI-3K) activity. Although PI-3K often contributes to cell survival and is active constitutively in LNCaP cells (21, 22), the lack of effect of LY294002 on LNCaP cells in serum-containing medium is in agreement with previous studies (22). It was also found that CKIs do not inhibit AKT activity in LNCaP cells (data not shown).

Figure 2:
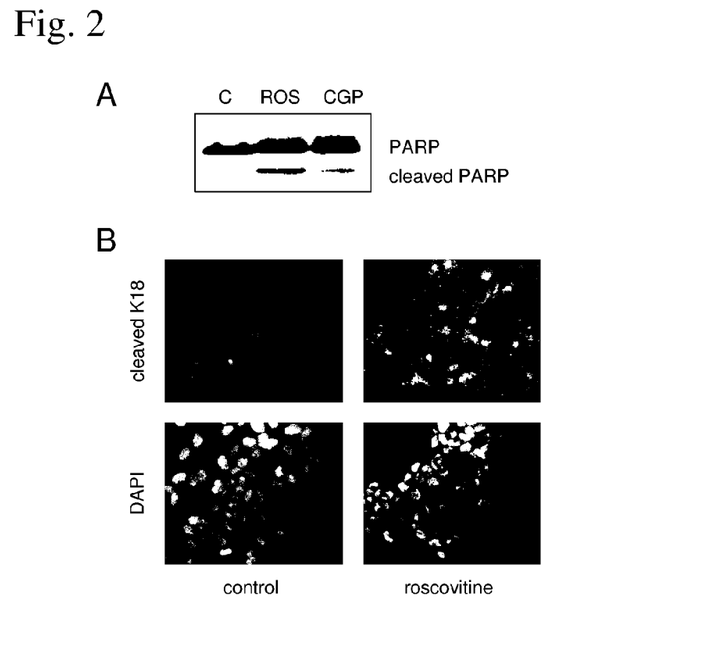

Collectively, the data in FIG. 1 show that CKIs induce the apoptosis of LNCaP cells. As further indication of DNA fragmentation in CKI-treated LNCaP cells, it was also found the following: One, DNA from control cells migrated as a single band on agarose gels, whereas DNA from CKI-treated cells migrated as a series of smaller-sized bands (i.e., was laddered, data not shown). Two, as determined by flow cytometry, >20% of CKI-treated cells contained a <2N content of DNA as compared with 1% of control cells (data not shown). In all experiments, apoptosis was maximal 20 hr after addition of CKIs to cells (data not shown). Additional studies demonstrated apoptosis of LNCaP-Rf cells by CKIs. These androgen-independent cells were established by others by long-term culture of LNCaP cells in the absence of androgens (23). They express wild-type p53, as do LNCaP cells. The data in FIG. 2A show PARP cleavage in LNCaP-Rf cells exposed to 25 micro-M roscovitine or 5 micro-M CGP74514A for 20 hr. The data in FIG. 2B show keratin 18 cleavage in roscovitine-treated LNCaP-Rf cells. Apoptosis of CKI-treated LNCaP-Rf cells indicates that CKIs induce apoptosis in a manner unrelated to androgen dependence.

CKI-induced Apoptosis of LNCaP Cells Requires Caspase-9 and Caspase-3 Activity.

Figure 3:
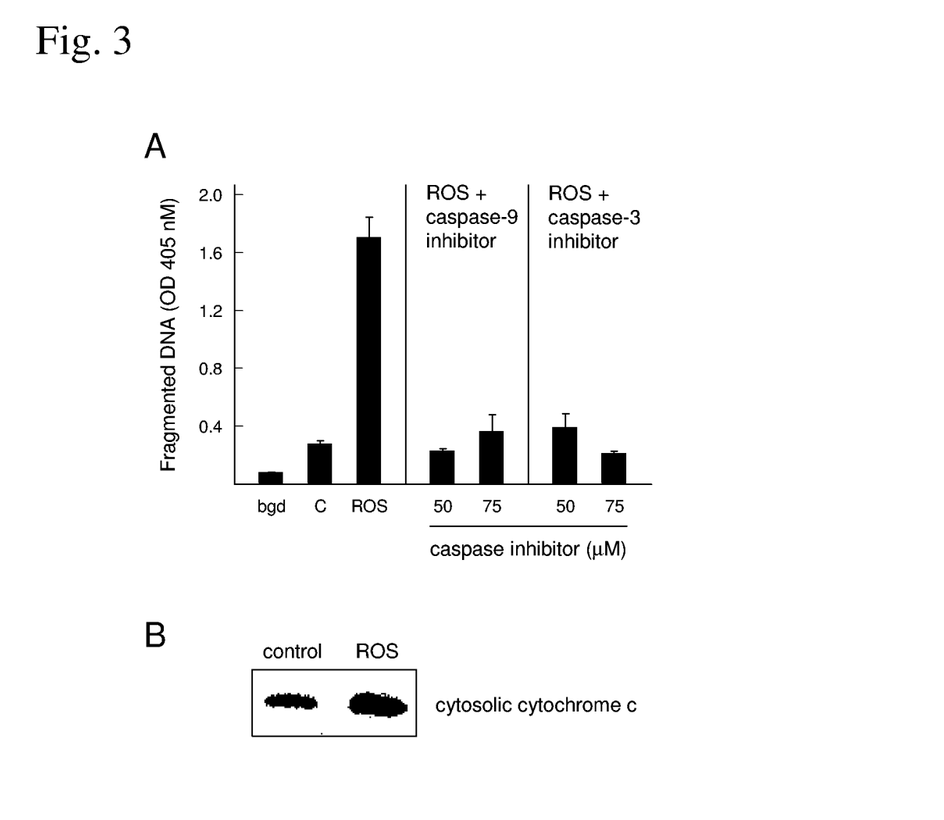

To identify the caspases that become active in LNCaP cells exposed to CKIs, cells were co-treated with roscovitine and a caspase-9 inhibitor (z-LEHD-fmk) or a caspase-3 inhibitor (z-DEVD-fmk) for 20 hr. Apoptosis was monitored by the DNA fragmentation assay. As shown in FIG. 3A, roscovitine did not induce apoptosis when presented to cells in combination with either inhibitor. Thus, the roscovitine-induced apoptosis of LNCaP cells requires caspase-9 activity and caspase-3 activity. The near complete rescue of LNCaP cells by the caspase-9 inhibitor suggests that CKIs activate primarily (if not exclusively) the mitochondrial pathway of apoptosis.

To provide further evidence of mitochondrial dysfunction, amounts of cytochrome c in mitochondria-free cytosolic extracts prepared from LNCaP cells treated with or without roscovitine for 20 hr were compared. As shown in FIG. 3B, cytochrome c was present in the cytosol of roscovitine-treated cells but was not detectable in the cytosol of control cells.

CKIs Increase the Abundance of p53 and Reduce the Abundance of XIAP in LNCaP cells.

Figure 4:
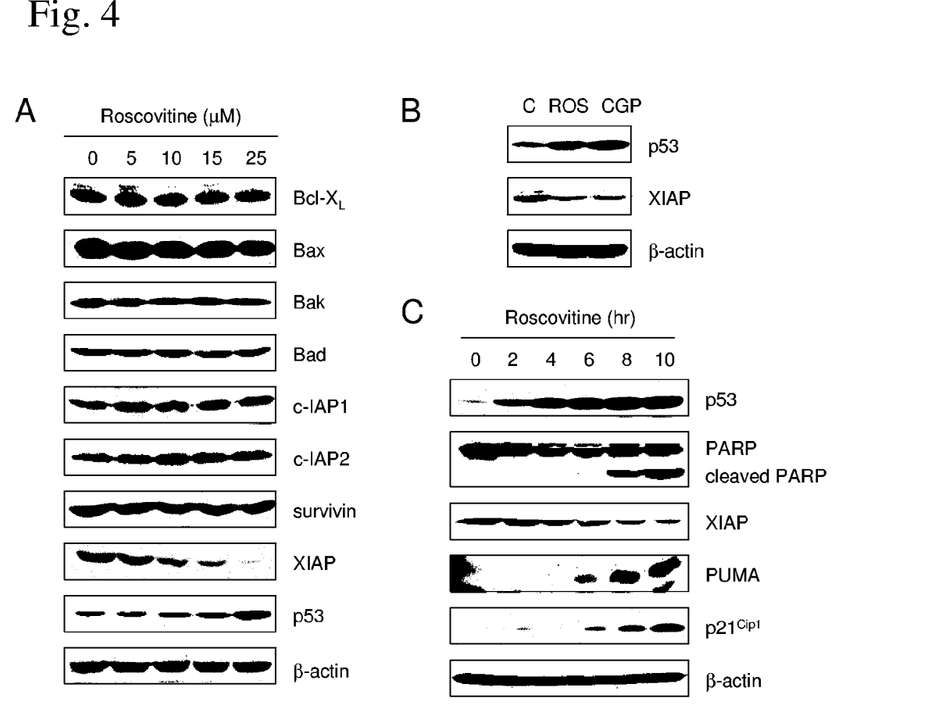
FIG. 4 shows p53 accumulation and XIAP depletion in CKI-treated LNCaP and LNCaP-Rf cells. (A) LNCaP cells received the indicated amounts of roscovitine for 20 hr. (B) LNCaP-Rf cells received DMSO (control, C), 25 micro-M roscovitine (ROS), or 5 micro-M CGP74514A (CGP) for 20 hr. (C) LNCaP cells received 25 micro-M roscovitine for times indicated. A, B, C, Protein abundance was determined by Western blotting of cell extracts. beta-actin serves as the loading control.

Toward the goal of determining the mechanism of CKI-induced apoptosis, amounts of several apoptosis-regulatory proteins in CKI-treated cells were monitored by Western blotting. Exposure of LNCaP cells to roscovitine (5 micro-M to 25 micro-M) for 20 hr had no effect on the abundance of Bcl-$X_L$, Bax, Bak, Bad, c-IAP-1, c-IAP-2, or survivin (FIG. 4A). Amounts of Bcl-2 were also unaffected by roscovitine (data not shown). On the other hand, amounts of XIAP declined >90% in cells receiving 25 CM roscovitine. Conversely, and in agreement with studies of other cell types (4, 8, 9, 24, 25), p53 increased in abundance in roscovitine-treated LNCaP cells. Similar results were obtained in LNCaP-Rf cells exposed to roscovitine or CGP74514A (FIG. 4B and data not shown).

The kinetics of p53 accumulation, XIAP depletion, and PARP cleavage in roscovitine-treated LNCaP cells are shown in FIG. 4C. p53 abundance increased within 2 hr of addition of roscovitine to cells and was maximal at 4 hr. p53 accumulation preceded PARP cleavage, which began 6 to 8 hr after roscovitine addition and increased thereafter. Increases in amounts of cleaved PARP paralleled decreases in amounts of XIAP. These kinetics are consistent with a model of apoptosis in which accumulation of the apoptotic protein p53 and loss of the anti-apoptotic protein XIAP signal the death of CKI-treated prostate cancer cells.

p53-responsive genes include those encoding PUMA and the cell cycle inhibitor p21$^{Cip1}$ (16, 26). Consistent with transcriptional activation of p53, both proteins accumulated in roscovitine-treated LNCaP cells, albeit with delayed kinetics relative to p53 accumulation (FIG. 4C). Delayed increases in p21$^{Cip1}$ abundance in roscovitine-treated MCF-7 cells have been observed previously (9).

Efficient Apoptosis of Prostate Cancer Cells Requires p53 Accumulation.

Figure 5:
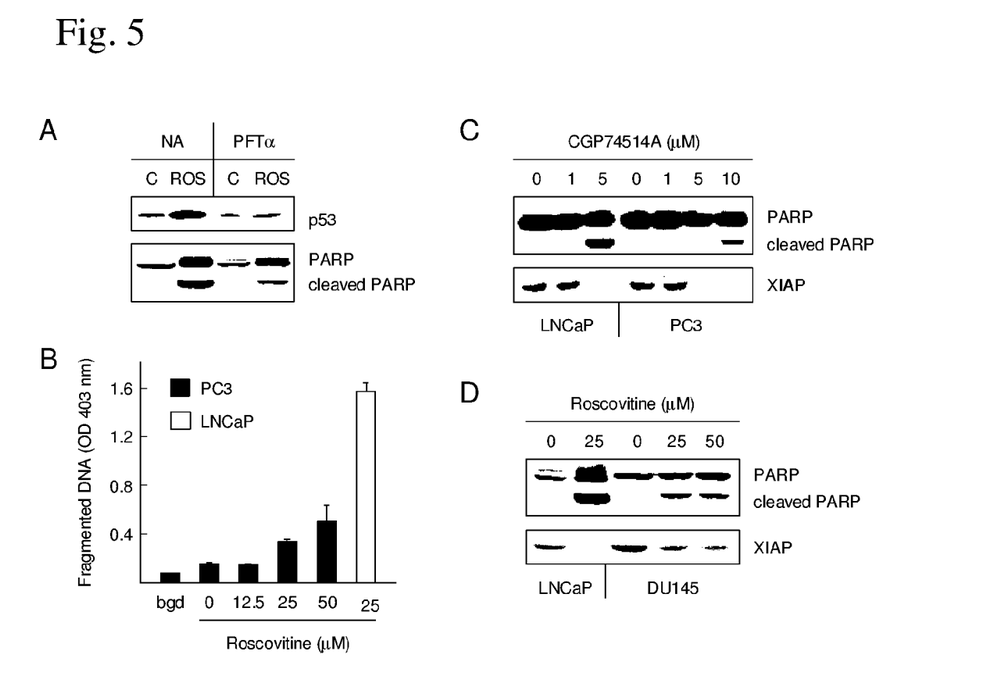

The data presented above suggest that CKIs induce the apoptosis of LNCaP and LNCaP-Rf cells by increasing amounts of p53 and/or by decreasing amounts of XIAP. To assess the p53-dependence of CKI-induced apoptosis, two sets of experiments were performed. First, LNCaP cells were treated with roscovitine in the presence and absence of pifithrin-α, a compound that inhibits the accumulation and/or the transcriptional activity of p53 (27-29). As shown in FIG. 5A, p53 abundance did not increase in LNCaP cells co-treated with roscovitine and pifithrin-α. Importantly, pifithrin-α substantially reduced (but did not eliminate) PARP cleavage in roscovitine-treated cells. Thus, efficient apoptosis of LNCaP cells by CKIs requires increases in p53 abundance.

Second, prostate cancer cells that do not express p53 (PC3) or express mutant p53 (DU145) were exposed to CKIs for 20 hr. Such treatment produced small increases in amounts of fragmented DNA (FIG. 5B) and cleaved PARP (FIG. 5C, D). Overall, PC3 and DU145 cells were much less susceptible to CKI-induced apoptosis than were LNCaP cells. For example, amounts of fragmented DNA increased 8-fold in PC3 cells receiving 25 micro-M roscovitine but only 3-fold in PC3 cells receiving 50 micro-M roscovitine (FIG. 5B). Exposure of PC3 and DU145 cells to CKIs for time periods greater than 20 hr did not further increase DNA fragmentation or PARP cleavage (data not shown).

Collectively, the data in FIG. 5 demonstrate the p53 dependence of CKI-elicited prostate cell apoptosis. Of interest, the data in FIGS. 5C and D show robust reductions in XIAP abundance in PC3, DU145, and LNCaP cells in response to CKIs. This finding indicates that CKIs down-regulate XIAP by a p53-independent mechanism and that reductions in XIAP abundance are insufficient for maximal apoptosis.

XIAP Depletion Accelerates p53-induced Apoptosis of Prostate Cancer Cells.

Figure 6:
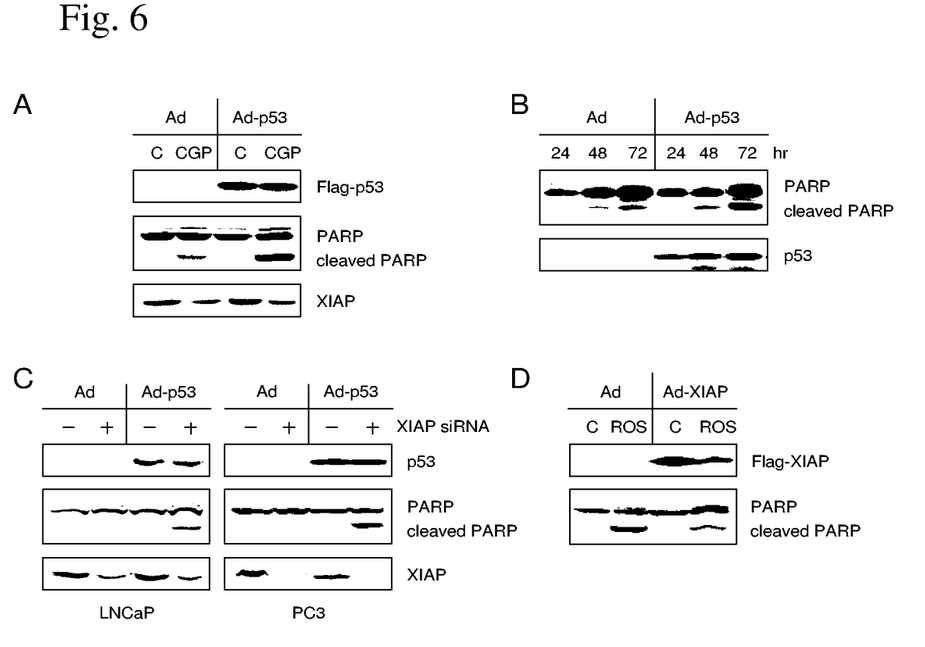
Figure 7:
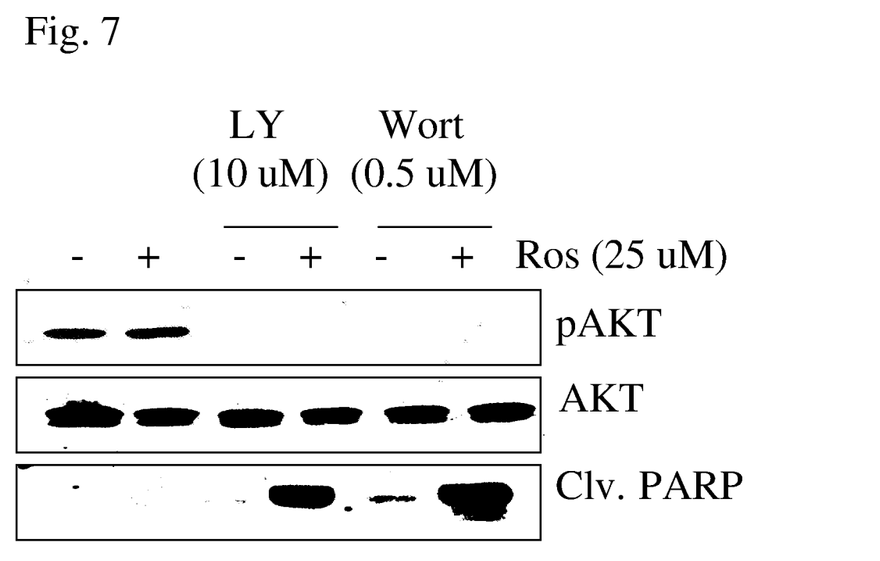
FIG. 7 shows increased apoptosis of LnCaP cells when treated with roscovitine in combination with a PI3K inhibitor. Cells were pre-treated with either 10 uM of LY294002 or 0.5 uM of Wortmanin for 1 hr and then cultured in presence or absence of 25 uM roscovitine for 8 hours and PARP cleavage was measured by Western blotting.
Figure 8:
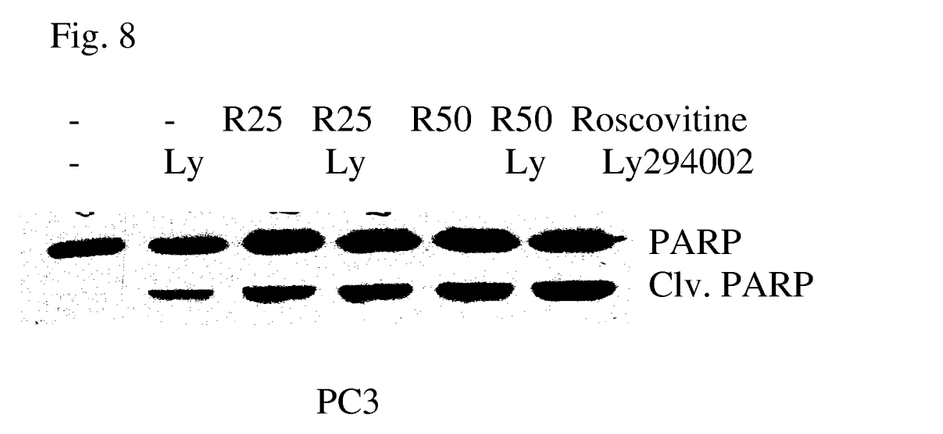
FIG. 8 shows increased apoptosis of PC3 cells when treated with roscovitine in combination with a PI3K inhibitor. Cells were pre-treated with either 10 uM of LY294002 for 1 hr and then cultured in presence or absence of indicated concentrations of roscovitine for 24 hours and PARP cleavage was measured by Western blotting.

Although required for CKI-induced apoptosis, p53 accumulation may be insufficient. To assess sufficiency, we infected PC3 cells with adenovirus alone (control) or adenovirus encoding wild-type Flag-tagged p53 (Ad-p53). Twenty-four hours after addition of virus, cells received vehicle or CGP74514A; cells were harvested 20 hr thereafter (44 hr after addition of virus). Cells infected with Ad-p53 expressed Flag-p53 but did not apoptose (as monitored by PARP cleavage) in the absence of CGP7451A (FIG. 6A). Although not apoptotic in these conditions, Ad-p53 sensitized PC3 cells to CKI-induced apoptosis; as shown in FIG. 6A, cells receiving both Ad-p53 and CGP74514A contained more cleaved PARP than did cells receiving CGP74514A alone. These data suggest that p53 accumulation induces apoptosis in conjunction with additional CKI-elicited events. The data in FIG. 6A also show that ectopic expression of p53 does not reduce XIAP abundance, and results similar to those in FIG. 6A were obtained in experiments on DU145 cells (data not shown).

Additional experiments demonstrated PARP cleavage in PC3 cells exposed to Ad-p53 for 72 hr (FIG. 6B). In agreement with the data in FIG. 6A, Ad-p53 did not increase amounts of cleaved PARP (relative to control virus) when presented to cells for 24 or 48 hr. p53 was expressed in Ad-p53-infected cells at all time points. Thus, given enough time, ectopic p53 is apoptotic per se; however, it is a more efficient inducer of apoptosis presented to cells in combination with CKIs.

CKIs may expedite p53-mediated apoptosis by reducing the abundance of XIAP. To test this hypothesis, we infected LNCaP and PC3 cells with Ad-p53, adenovirus encoding XIAP siRNA (Ad-siXIAP), or both. Cells expressing Ad-p53 expressed supranormal amounts of p53, and expression of Ad-siXIAP substantially reduced XIAP abundance (FIG. 6C). Infection of cells with Ad-p53 or Ad-siXIAP for 40 hr did not induce apoptosis; however, cells readily apoptosed when co-infected with both viruses. These results suggest that apoptosis of prostate cancer cells by CKIs results from a combination of p53 accumulation and XIAP depletion.

As shown in FIG. 6D, overexpression of XIAP reduced the extent to which LNCaP cells apoptosed when exposed to roscovitine. This finding confirms the capacity of XIAP to promote the survival of CKI-treated prostate cancer cells. Overexpression of XIAP has been shown to inhibit the apoptosis of LNCaP cells by taxol and cisplatin (30, 31), as well as the apoptosis of other cancer cell types by various death stimuli (32-35).

Discussion

The data presented herein shows that CKIs induce the apoptosis of prostate cancer cells that express wild-type p53 (LNCaP and LNCaP-Rf). CKIs activate the mitochondrial pathway of apoptosis in these cells, as indicated by: one, the abrogation of CKI-induced apoptosis by an inhibitor of caspase-9, and two, the presence of cytochrome c in the cytosol of CKI-treated cells. Amounts of p53 increased substantially in cells exposed to CKIs, whereas amounts of XIAP decreased. We suggest that these two events account in large part for the apoptotic effects of CKIs on prostate cancer cells.

Maximal apoptosis of prostate cancer cells by CKIs required the accumulation of wild-type p53. First, pifithrin-alpha prevented p53 accumulation and inhibited apoptosis when added to LNCaP cells in combination with roscovitine. Others observed similar effects of pifithrin-alpha in 5-azacytidine-treated colon cancer cells and doxirubucin-treated endothelial cells (28, 29). Second, p53-deficient prostate cancer cells (PC3 and DU145) apoptosed to a much lesser extent when exposed to CKIs than did LNCaP cells. PC3 and DU145 cells were not, however, completely resistant to CKI-induced apoptosis nor were pifithrin-alpha-treated LNCaP cells. Thus, CKIs also induce apoptosis—albeit ineffectively—by a p53-independent mechanism. Whether this mechanism involves other members of the p53 family remains to be determined.

Prostate cancer cells ectopically expressing p53 or depleted of XIAP by RNA interference did not apoptose, as monitored 40 to 44 hr after infection. Thus, within this time frame, neither event is sufficient for apoptosis. On the other hand, cells efficiently apoptosed within 44 hr when co-infected with both Ad-p53 and Ad-XIAP siRNA. These findings show that p53 accumulation and XIAP depletion—both of which occur in CKI-treated cells—recapitulate the apoptotic actions of CKIs. We note that these events are independent—XIAP depletion does not alter p53 abundance, ectopic expression of p53 does not alter XIAP abundance, and CKIs reduce XIAP abundance in the absence of functional p53.

PC3 cells apoptosed when exposed to Ad-p53 alone for 72 hr. Thus, in agreement with several previous studies on prostate cancer cells (36-40), p53 can induce apoptosis by itself. However, as shown here, XIAP depletion clearly accelerates the onset of p53-induced apoptosis. Insufficiency of p53 accumulation and of XIAP loss for apoptosis is supported by other studies. Colletier et al. (41) showed that Ad-p53 sensitized LNCaP cells to radiation-induced death but was not apoptotic per se. Amantana et al. (42) found that XIAP depletion was weakly apoptotic for DU145 cells but synergized with cisplatin (41). Carson et al. (43) demonstrated caspase activation in LNCaP cells microinjected with both cytochrome c and Smac but not with either alone (36). Smac binds and inactivates IAPs (11), and XIAP is the predominant Smac binding partner in LNCaP cells (43).

CKIs inhibit the activity of cdk2, cdk1 and cdk7 (1-3). Which of these kinases (if any) modulates the abundance of p53 and XIAP—and how it does so—remains to be determined. cdk7 promotes transcriptional elongation by phosphorylating RNA polymerase II (44). Thus, ablation of cdk7 activity by CKIs may impede production of the transcripts for XIAP and for Mdm2, the protein that signals p53 destruction (45). Consistent with this hypothesis, we and others observed reduced amounts of XIAP mRNA and Mdm2 mRNA in roscovitine-treated MT-2 and MCF-7 cells, respectively (8, 9). cdk2 and cdk1 phosphorylate p53 at serine 315 (46-48), and studies by Sakaguchi et al. (49) suggest that p53 degrades more rapidly when phosphorylated at this site. On the other hand, replacement of serine 315 with alanine did not negate p53 accumulation in roscovitine-treated MCF-7 cells (9). Although cdk7 also phosphorylates p53 (50, 51), its effects on p53 half-life are not known.

REFERENCES

1. Meijer L, Borgne A, Mulner O, et al. Biochemical and cellular effects of roscovitine, a potent and selective inhibitor of the cyclin-dependent kinases cdc2, cdk2 and cdk5. Eur J Biochem 1997; 243:527-536.
2. McClue S J, Blake D, Clarke R, et al. In vitro and in vivo antitumor properties of the cyclin dependent kinase inhibitor CYC202 (R-roscovitine). Int J Cancer 2002; 102:463-468.
3. Imbach P, Capraro H G, Furet P, Mett H, Meyer T, Zimmermann J. 2,6,9-trisubstituted purines: optimization towards highly potent and selective CDK1 inhibitors. Bioorg Med Chem Lett 1999; 9:91-96.
4. David-Pfeuty T. Potent inhibitors of cyclin-dependent kinase 2 induce nuclear accumulation of wild-type p53 and nucleolar fragmentation in human untransformed and tumor-derived cells. Oncogene 1999; 18:7409-7422.
5. Mihara M, Shintani S, Kiyota A, Matsumura T, and Wong D T. Cyclin-dependent kinase inhibitor (roscovitine) suppresses growth and induces apoptosis by regulating Bcl-x in head and neck squamous cell carcinoma cells. Int J Oncol 2002; 21:95-101.
6. Wojciechowski J, Horky M, Gueorguieva M, Wesierska-Gadek J. Rapid onset of nucleolar disintegration preceding cell cycle arrest in roscovitine-induced apoptosis of human MCF-7 breast cancer cells. Int J Cancer 2002; 106:486-495.
7. Dai Y, Dent P, Grant S. Induction of apoptosis in human leukemia cells by the CDK1 inhibitor CGP74514A. Cell Cycle 2002; 1:143-152.
8. Mohapatra S, Chu B, Wei S, et al. Roscovitine inhibits STAT5 activity and induces apoptosis in the human leukemia virus type 1-transformed cell line MT-2. Cancer Res 2003; 63:8523-8530.
9. Lu W, Chen L, Peng Y, Chen J. Activation of p53 by roscovitine-mediated suppression of MDM2 expression. Oncogene 2001; 20:3206-3216.
10. Strasser A, O'Connor L, Dixit V M. Apoptosis signaling. Annu Rev Biochem 2000; 69:217-245.
11. Vaux D L, Silke J. Mammalian mitochondrial IAP binding proteins. Biochem Biophys Res Commun 2003; 304:499-504.
12. Deveraux Q L, Roy N, Stennicke H R, et al. IAPs block apoptotic events induced by caspase-8 and cytochrome c by direct inhibition of distinct caspases. Embo J 1998; 17:2215-2223.
13. Borner C. The Bcl-2 protein family: sensors and checkpoints for life-or-death decisions. Mol Immunol 2003; 39:615-647.
14. Fridman J S, Lowe S W. Control of apoptosis by p53. Oncogene 2003; 22:9030-9040.
15. Miyashita T, Reed J C. Tumor suppressor p53 is a direct transcriptional activator of the human bax gene. Cell 1995; 80:293-299.
16. Nakano K, Vousden K H. PUMA, a novel proapoptotic gene, is induced by p53. Mol Cell 2001; 7:683-694.
17. Oda E, Ohki R, Murasawa H, et al. Noxa, a BH3-only member of the Bcl-2 family and candidate mediator of p53-induced apoptosis. Science 2000; 288:1053-1058.
18. Murphy M E, Leu J I, George D L. p53 moves to mitochondria: a turn on the path to apoptosis. Cell Cycle 2004; 3:836-839.
19. Hollstein M, Sidransky D, Vogelstein B, Harris C C. p53 mutations in human cancers. Science 1991; 253:49-53.
20. Leers M P, Kolgen W, Bjorklund V, et al. Immunocytochemical detection and mapping of a cytokeratin 18 neo-epitope exposed during early apoptosis. J Pathol 1999; 187:567-572.
21. Cantley L C. The phosphoinositide 3-kinase pathway. Science 2002; 296:1655-1657.
22. Carson J P, Kulik G, Weber M J. Antiapoptotic signaling in LNCaP prostate cancer cells: a survival signaling pathway independent of phosphatidylinositol 3'-kinase and Akt/protein kinase B. Cancer Res 1999; 59:1449-1453.
23. Zegarra-Moro O L, Schmidt L J, Huang H, Tindall D J. Disruption of androgen receptor function inhibits proliferation of androgen-refractory prostate cancer cells. Cancer Res 2002; 62:1008-1013.
24. Blaydes J P, Craig A L, Wallace M, et al. Synergistic activation of p53-dependent transcription by two cooperating damage recognition pathways. Oncogene 2000; 19:3829-3839.
25. Kim E H, Kim S U, Shin D Y, Choi K S. Roscovitine sensitizes glioma cells to TRAIL-mediated apoptosis by downregulation of survivin and XIAP. Oncogene 2004; 23:446-456.
26. el-Deiry W S, Tokino T, Velculescu V E, et al. WAF1, a potential mediator of p53 tumor suppression. Cell 1993; 75:817-825.
27. Komarov P G, Komarova E A, Kondratov R V, et al. A chemical inhibitor of p53 that protects mice from the side effects of cancer therapy. Science 1999; 285:1733-1737.
28. Schneider-Stock R, Diab-Asseff M, Rohrbeck A, et al. 5-AZA-cytidine is a potent inhibitor of DNA methyltransferase 3a and induces apoptosis in HCT-116 colon cancer cells via Gadd45- and p53-dependent mechanisms. J Pharmacol Exp Ther 2004; in press.
29. Lorenzo E, Ruiz-Ruiz C, Quesada A J, et al. Doxorubicin induces apoptosis and CD95 gene expression in human primary endothelial cells through a p53-dependent mechanism. J Biol Chem 2002; 277:10883-10892.
30. Nomura T, Mimata H, Takeuchi Y, Yamamoto H, Miyamoto E, Nomura Y. The X-linked inhibitor of apoptosis protein inhibits taxol-induced apoptosis in LNCaP cells. Urol Res 2003; 31:37-44.
31. Nomura T, Mimata H, Yamasaki M, Nomura Y. Cisplatin inhibits the expression of X-linked inhibitor of apoptosis protein in human LNCaP cells. Urol Oncol 2004; 22:453-460.
32. Asselin E, Mills G B, Tsang B K. XIAP regulates Akt activity and caspase-3-dependent cleavage during cisplatin-induced apoptosis in human ovarian epithelial cancer cells. Cancer Res 2001; 61:1862-1868.
33. Li J, Feng Q, Kim J M, et al. Human ovarian cancer and cisplatin resistance: possible role of inhibitor of apoptosis proteins. Endocrinology 2001; 142:370-380.
34. Duckett C S, Li F, Wang Y, Tomaselli K J, Thompson C B, Armstrong R C. Human IAP-like protein regulates programmed cell death downstream of Bcl-xL and cytochrome c. Mol Cell Biol 1998; 18:608-615.

35. Holcik M, Yeh C, Korneluk R G, Chow T. Translational upregulation of X-linked inhibitor of apoptosis (XIAP) increases resistance to radiation induced cell death. Oncogene 2000; 19:4174-4177.
36. Hara I, Miyake H, Hara S, Arakawa S, Kamidono S. Differential involvement of the Fas receptor/ligand system in p53-dependent apoptosis in human prostate cancer cells. Prostate 2000; 45:341-349.
37. Srivastava S, Katayose D, Tong Y A, et al. Recombinant adenovirus vector expressing wild-type p53 is a potent inhibitor of prostate cancer cell proliferation. Urology 1995; 46:843-848.
38. Roy I, Holle L, Song W, Holle E, Wagner T, Yu X. Efficient translocation and apoptosis induction by adenovirus encoded VP22-p53 fusion protein in human tumor cells in vitro. Anticancer Res 2002; 22:3185-3189.
39. Davies M A, Koul D, Dhesi H, et al. Regulation of Akt/PKB activity, cellular growth, and apoptosis in prostate carcinoma cells by MMAC/PTEN. Cancer Res 1999; 59:2551-2556.
40. Schumacher G, Bruckheimer E M, Beham A W, et al. Molecular determinants of cell death induction following adenovirus-mediated gene transfer of wild-type p53 in prostate cancer cells. Int J Cancer 2001; 91:159-166.
41. Colletier P J, Ashoori F, Cowen D, et al. Adenoviral-mediated p53 transgene expression sensitizes both wild-type and null p53 prostate cancer cells in vitro to radiation. Int J Radiat Oncol Biol Phys 2000; 48:1507-1512.
42. Amantana A, London C A, Iversen P L, Devi G R. X-linked inhibitor of apoptosis protein inhibition induces apoptosis and enhances chemotherapy sensitivity in human prostate cancer cells. Mol Cancer Ther 2004; 3:699-707.
43. Carson J P, Behnam M, Sutton J N, et al. Smac is required for cytochrome c-induced apoptosis in prostate cancer LNCaP cells. Cancer Res 2002; 62:18-23.
44. Dahmus M E. Reversible phosphorylation of the C-terminal domain of RNA polymerase II. J Biol Chem 1996; 271:19009-19012.
45. Moll U M, Petrenko O. The MDM2-p53 interaction. Mol Cancer Res 2003; 1:1001-1008.
46. Price B D, Hughes-Davies L, Park S J. Cdk2 kinase phosphorylates serine 315 of human p53 in vitro. Oncogene 1995; 11:73-80.
47. Wang Y, Prives C. Increased and altered DNA binding of human p53 by S and $G_2/M$ but not $G_1$ cyclin-dependent kinases. Nature 1995; 376:88-91.
48. Bischoff J R, Friedman P N, Marshak D R, Prives C, Beach D. Human p53 is phosphorylated by p60-cdc2 and cyclin B-cdc2. Proc Natl Acad Sci USA 1990; 87:4766-4770.
49. Sakaguchi K, Sakamoto H, Xie D, et al. Effect of phosphorylation on tetramerization of the tumor suppressor protein p53. J Protein Chem 1997; 16:553-556.
50. Ko L J, Shieh S Y, Chen X, et al. p53 is phosphorylated by CDK7-cyclin H in a p36$^{MAT1}$-dependent manner. Mol Cell Biol 1997; 17:7220-7229.
51. Lu H, Fisher R P, Bailey P, Levine A J. The CDK7-cycH-p36 complex of transcription factor IIH phosphorylates p53, enhancing its sequence-specific DNA binding activity in vitro. Mol Cell Biol 1997; 17:5923-5934.
52. Siddiqui E, Mumtaz F H, Gelister J. Understanding prostate cancer. J R Soc Health 2004; 124:219-221.

What is claimed is:

1. A method for treating prostate cancer in a subject in need thereof comprising:
    obtaining a sample from the subject;
    assaying the sample for the expression of p53;
    detecting expression of p53 in the sample; and
    administering a therapeutically effective amount of a compound selected from the group consisting of CGP74514A, roscovitine and R-roscovitine;
    whereby the compound is administered to the subject subsequently to the detection of p53.

2. The method of claim 1 wherein the compound is a therapeutically effective amount of roscovitine or a pharmaceutically acceptable salt thereof.

3. The method of claim 1 wherein the prostate cancer is advanced prostate cancer characterized by androgen-independence.

4. The method of claim 1 wherein the prostate cancer cells express wild-type p53.

5. The method of claim 1 wherein the compound is administered in combination with an additional agent selected from the group consisting of LY294002 and Wortmannin.

6. The method of claim 1 wherein the compound is administered with at least one additional component selected from the group consisting of a pharmaceutically acceptable carrier, a diluent and an excipient.

7. A method for inducing apoptosis in at least one prostate cancer cell in a population comprising:
    obtaining a sample from the population;
    assaying the sample for expression of p53;
    detecting expression of p53 in the sample; and contacting the cell population with a compound selected from the group consisting of CGP74514A, roscovitine and R-roscovitine;

whereby the compound contacts the cell population subsequently to the detection of p53 in the sample.

8. The method of claim 7 wherein the compound is a therapeutically effective amount of roscovitine or a pharmaceutically acceptable salt thereof.

9. The method of claim 7 wherein the compound is administered in combination with an additional agent selected from the group consisting of LY294002 and Wortmannin.

10. A method for treating prostate cancer in a subject in need thereof comprising:
    obtaining a sample from the subject;
    assaying the sample for the presence of p53;
    detecting expression of p53 in the sample; and
    administering a therapeutically effective amount of a compound selected from the group consisting of CGP74514A, roscovitine and R-roscovitine and a vector encoding p53 to the subject;

whereby the compound and vector are administered to the subject subsequently to the detection of p53 in the sample.

11. The method of claim 10, wherein the vector encoding p53 is an adenovirus vector encoding p53.

12. The method of claim 10 wherein the p53-encoding vector is an adenovirus vector encoding wild-type p53.

13. The method of claim 10, further comprising administering a therapeutically effective amount of a vector which inhibits XIAP to the subject responsive to the absence of p53 in the sample.

14. The method of claim 13, wherein the vector which inhibits XIAP is an adenovirus vector encoding XIAP siRNA.

* * * * *

UNITED STATES PATENT AND TRADEMARK OFFICE
CERTIFICATE OF CORRECTION

PATENT NO. : 8,716,299 B2
APPLICATION NO. : 11/306241
DATED : May 6, 2014
INVENTOR(S) : Subhra Mohapatra et al.

It is certified that error appears in the above-identified patent and that said Letters Patent is hereby corrected as shown below:

In the Specification

Column 1, lines 15-17, the Statement of Government Interest should be changed to "This invention was made with Government support under Grant No. R01-CA093544 awarded by the National Institutes of Health. The Government has certain rights in the invention".

Signed and Sealed this
Fifth Day of August, 2014

Michelle K. Lee
*Deputy Director of the United States Patent and Trademark Office*

```
                        SEQUENCE LISTING

<160> NUMBER OF SEQ ID NOS: 1

<210> SEQ ID NO 1
<211> LENGTH: 55
<212> TYPE: DNA
<213> ORGANISM: Homo sapiens

<400> SEQUENCE: 1
ggcaggttgt agatatatca gctcgagctg atatatctac aacctgccct ttttg        55
```